United States Patent [19]
Yao et al.

[11] Patent Number: 5,482,677
[45] Date of Patent: Jan. 9, 1996

[54] THERMALLY DESORBABLE PASSIVE DOSIMETER

[75] Inventors: Chaoliang Yao, Missouri City; Dennis C. Krueger, Richmond, both of Tex.

[73] Assignee: Shell Oil Company, Houston, Tex.

[21] Appl. No.: 62,085

[22] Filed: May 14, 1993

[51] Int. Cl.$^6$ .............................. G01N 1/22; G01N 7/04
[52] U.S. Cl. ....................... 422/88; 422/83; 73/23.39; 73/23.42; 73/31.07; 73/863.21; 436/178; 210/198.3
[58] Field of Search .................. 422/88, 83, 68.1, 422/69; 73/31.07, 23.39, 23.42, 863.21; 55/158, 197; 436/178; 210/198.3, 658

[56] References Cited

U.S. PATENT DOCUMENTS

| | | | |
|---|---|---|---|
| 4,040,805 | 8/1977 | Nelms et al. | 55/158 |
| 4,267,023 | 5/1981 | Frant et al. | 422/88 X |
| 4,327,575 | 5/1982 | Locker | 73/23 |
| 4,350,037 | 9/1982 | Higham | 73/23 |
| 4,389,372 | 6/1983 | Lalin | 422/88 |
| 4,528,160 | 7/1985 | Eckstein et al. | 422/86 |
| 4,636,227 | 1/1987 | Yin et al. | 55/74 |
| 4,759,210 | 7/1988 | Wohltjem | 73/31.07 X |
| 4,766,760 | 8/1988 | Poshemansky et al. | 73/23.1 |
| 4,772,560 | 9/1988 | Attar | 436/165 |
| 4,946,649 | 8/1990 | Pannwitz | 422/60 |
| 5,027,643 | 7/1991 | Jenkins | 73/23.39 |
| 5,168,068 | 12/1992 | Yanagisawa et al. | 436/134 |

FOREIGN PATENT DOCUMENTS 3729891  3/1989  Germany.

OTHER PUBLICATIONS

Abstract No. 129, Salt Palace Center Abstract Book, May 18–24, 1991.

Macleod, G. and Ames, J. M., "Comparative Assessment of The Artefact Background On Thermal Desorption of TENAX GC and TENAX TA", *Journal of Chromatography*, 393–398 (1986).

Fields, B., "Diffusive Sampling Onto Solid Adsorbents For The Analysis of Benzene And 1,3–Butadiene In Air By Gas Chromatogrpahy", *Diffusive Sampling an Alternative Approach to Workplace Air Monitoring*, A. Berlin, R. H. Brown, K. J. Saunders, Eds., Royal Society Chemistry, London (1987) pp. 85–88.

Yin, C. C. and Layton–Matthews, G., "Development Of A Passive Sampler For Monitoring Ambient Levels of Organic Vapours Particularly Benzene" *Diffusive Sampling–an Alternative Approach to Workplace Air Monitoring*, A. Berlin, R. H. Brown, K. J. Saunders, Eds., Royal Society Chemistry, London (1987) pp. 78–81.

De Bortoli, M., Knoppel, H., Pecchio, E., and Vissers, H., "Performance of A Thermally Desorbable Diffusion Sampler For Personal And Indoor Air Monitoring" *Environment International*, vol. 15, pp. 427–434, (1989).

*Primary Examiner*—James C. Housel
*Assistant Examiner*—Harold Y. Pyon

[57] ABSTRACT

A passive dosimeter with a structurally reinforced sorbent wafer is used for monitoring a worker's exposure to ambient aromatics (benzene, toluene, ethylbenzene and xylenes). The wafer is preferably formed by pressing 4 mg of sorbent material between two pieces of 100 mesh stainless steel wire gauze. The thickness of the formed pellet is about 1 mm. The wafer sorbent material design produces a much smaller background noise on gas chromatographic (GC) analysis and enhances the signal-to-noise ratio during the thermal desorption process. This enables the detection of a much lower concentration level of ambient air contaminants than other types of passive dosimeters designed for thermal desorption analysis.

8 Claims, 6 Drawing Sheets

THERMALLY DESORBABLE PASSIVE DOSIMETER

FIELD OF THE INVENTION

The invention relates to passive dosimeters, particularly to personal tube dosimeters used for determining a worker's exposure to, and ambient concentration of, aromatic compounds such as benzene, toluene, ethylbenzene and xylenes (BTEX) in the workplace.

BACKGROUND OF THE INVENTION

Dosimeters according to the invention can be used to replace either the current active sampling charcoal tube monitors, which need to be worn with sampling pumps and utilize solvent extraction for analysis, or the badge-type passive dosimeters, which require a solvent extraction procedure for sample analysis. The use of a sampling pump reduces a worker's mobility whereas the use of solvent extraction increases analysis time and exposes laboratory personnel to hazardous chemicals. The elimination of sampling pumps and solvent extraction techniques greatly simplifies the sample collection and analysis of ambient air aromatics for personal exposure monitoring. The analytical procedure is fully automated.

Assignee's current NIOSH Method 1501 for aromatic hydrocarbon sampling uses a charcoal packed glass tube as a sample collection trap. A small personal pump is connected to this charcoal tube and a known volume of air is drawn through the tube during sampling. The tube is then extracted with carbon disulfide (1 mL). A fraction of the extract (1–2 μL) is then injected into a gas chromatograph (GC) for analysis. Alternatively, a passive badge-type 3M 3500 Organic Vapor Monitor (OVM) can be used for BTEX sampling. This latter method eliminates the use of personal sampling pumps, but it still requires the use of a $CS_2$ extraction procedure.

There are several reports and articles in the literature on passive dosimeters of various designs. Some reported the use of Perkin-Elmer tube-type passive dosimeters with sorbent material sold under the trademark TENAX. However, all reported studies use a large amount of packing material to fill the dosimeter tube (~200 mg). None use a wafer type configuration of sorbent packing design. The large amount of packing tends to give a large background signal when analyzed by thermal desorption which decreases the detection limit of the method.

Applicants also acknowledge their use of a charcoal absorbent wafer in a Perkin-Elmer ATD-50 automatic thermal desorption system for detection of 1,3-butadiene. The wafer was cut from the charcoal disk taken from a 3M 3500 organic vapor monitor. Charcoal is used only for extremely volatile components and is not suitable for BTEX determination using thermal desorption methods. Also, the charcoal wafer has structural integrity and did not require wire gauze structural elements. This was reported as Abstract No. 129 in the Salt Palace Center Abstract Book, May 18 14 24, 1991.

The article by MacLeod G., and Ames, J. M., entitled "Comparative Assessment Of The Artifact Background On Thermal Desorption Of TENAX GC And TENAX TA" which appeared in the Journal of Chromatography, 355–398 (1986) discussed the use of passive dosimeter tubes with 200 mg TENAX sorbent material packing. The non-wafer design passive dosimeter reported in this article requires repeated special high temperature and long duration thermal cleaning to reduce the GC analysis background. An article by Fields, B., entitled "Diffusive Sampling Onto Solid Adsorbents For The Analysis Of Benzene And 1,3-Butadiene In Air By Gas Chromatography" appeared in Diffusive Sampling-An Alternative Approach to Workplace Air Monitoring, A. Berlin, R. H. Brown, K. J. Saunders, Eds., Royal Society Chemistry, London (1987) pp. 85 and reported the use of Perkin-Elmer tube-type passive dosimeters packed with sorbent material sold under the trademark POROPAK Q, for personal monitoring. The article by Yin, C. C. and Layton-Matthews, G., entitled "Development Of A Passive Sampler For Monitoring Ambient Levels Of Organic Vapours Particularly Benzene" also appearing in Diffusive Sampling-An Alternative Approach To Workplace Air Monitoring, A. Berlin, R. H. Brown, K. J. Saunders, Eds., Royal Society Chemistry, London (1987) pp. 78 reported a large diffusive surface area passive dosimeter with 200 mg of TENAX sorbent material packing for benzene monitoring. The article by De Bortoli, M., Knoppel, H., Pecchio, E. and Vissers, H., entitled "Performance Of A Thermally Desorbable Diffusion Sampler For Personal And Indoor Air Monitoring" appeared in Environment International, Vol. 15, pp 427–434, 1989 and reported the use of a 160 mm long glass tube filled with 25–100 mm length of sorbent material for personal and indoor air monitoring.

SUMMARY OF THE INVENTION

A passive dosimeter with a structurally reinforced sorbent wafer is used for monitoring a worker's exposure to ambient aromatics (benzene, toluene, ethylbenzene, and xylenes). The wafer is preferably formed by pressing 4 mg of TENAX sorbent material between two pieces of 100 mesh stainless steel wire gauze in a small die and press. The thickness of the formed wafer is about 1 mm. The wafer-type sorbent material design produces a much smaller background noise on gas chromatographic (GC) analysis and enhances the signal-to-noise ratio during the thermal desorption process. This enables the detection of a much lower concentration level of ambient air contaminants than other types of passive dosimeters designed for thermal desorption analysis. The pressed wafer also provides a much smoother diffusion surface for sample collection, thus generating much more uniform sample uptake rates for passive sampling.

Accordingly, an object of the invention is a dosimeter comprising a thermally desorbable absorbent material in a structurally reinforced wafer configuration.

Another object of the invention is a dosimeter comprising a wafer having either various phases (solid or liquid) of chromatographic sorbents on diatomaceous earth, porous polymer sorbents, synthetically produced potassium, sodium, or calcium forms of zeolites, activated carbon, or a synthetic spherical silica-based synthetic support with various chromatographic stationary phases bonded to it.

A still further object of the invention is a dosimeter wherein the wafer is comprised of a porous polymer material based on 2,6-diphenyl-p-phenylene oxide.

DETAILED DESCRIPTION OF THE INVENTION

A passive dosimeter comprising a thermally desorbable sorbent material in a structurally reinforced wafer configuration is used to determine the ambient concentration of benzene, toluene, ethylbenzene, and xylenes (BTEX) in the work place. Applicant's dosimeter is a significant advance over the previously reported tube or badge dosimeters. The new dosimeter utilizes a Perkin-Elmer automatic thermal desorption (ATD) tube packed with a structurally reinforced TENAX sorbent wafer for passive sampling of atmospheric BTEX concentrations. After sample collection for a specified time length, the dosimeter is thermally desorbed and analyzed by gas chromatography (GC).

The uptake rate of a compound is the key element used for calculation of the personal exposure to hazardous chemicals. The values of various uptake rates for different chemicals are generally evaluated in laboratories through exposure tests under various simulated field conditions, such as relative humidities, linear face velocities, dosimeter diffusive face orientations, sampling matrices, etc.

The uptake rate for passive dosimeters is defined as:

$$\text{Uptake Rate} = \frac{W}{PPM \times t} \quad (1)$$

where W is the mass loading in nanograms found on passive dosimeters, PPM is the exposed test concentration in parts per million, and t is the exposure time. The unit for the uptake rate is (nanograms)/(PPM)(min).

During the actual use of the passive dosimeter for exposure assessment, Equation 1 is used with the sampling time and the laboratory-determined uptake rates for calculation of the personal exposure to toxic chemicals.

Figure 1:
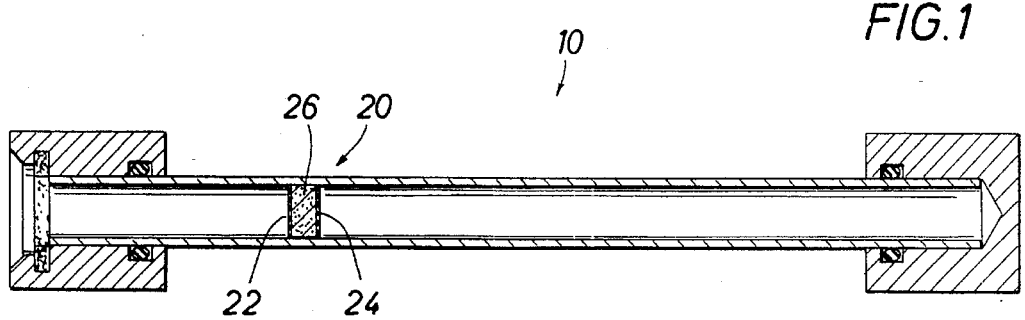
FIG. 1 is a cross section of a Passive Dosimeter according to the present invention.
Figure 2:
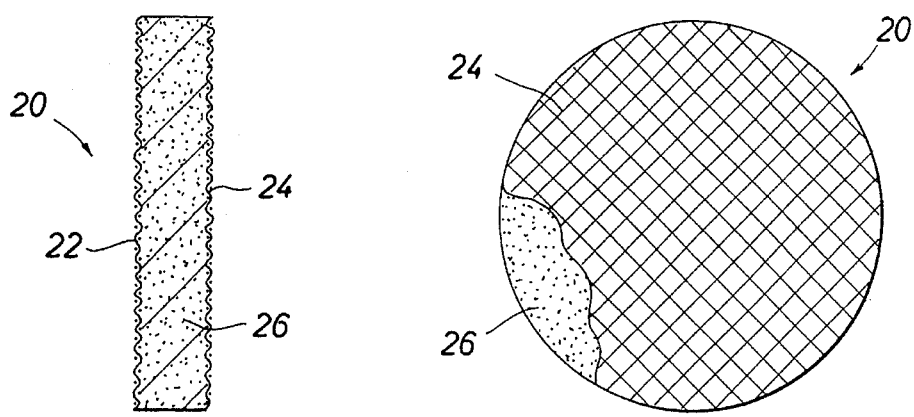
FIG. 2 is an illustration showing details of the structurally reinforced wafer used in the dosimeter of FIG. 1.
Figure 3:
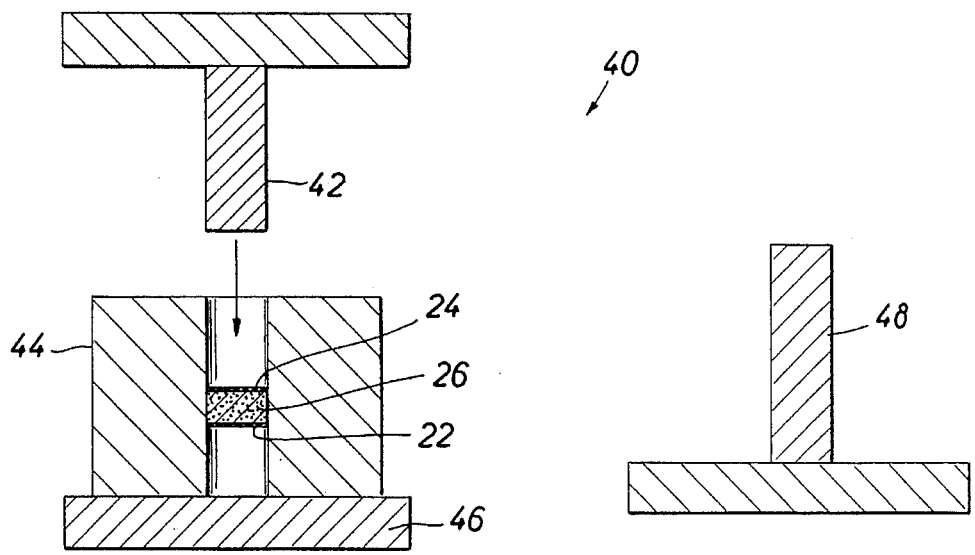
FIG. 3 illustrates the design of the die used in making the wafer of FIG. 3
Figure 4:
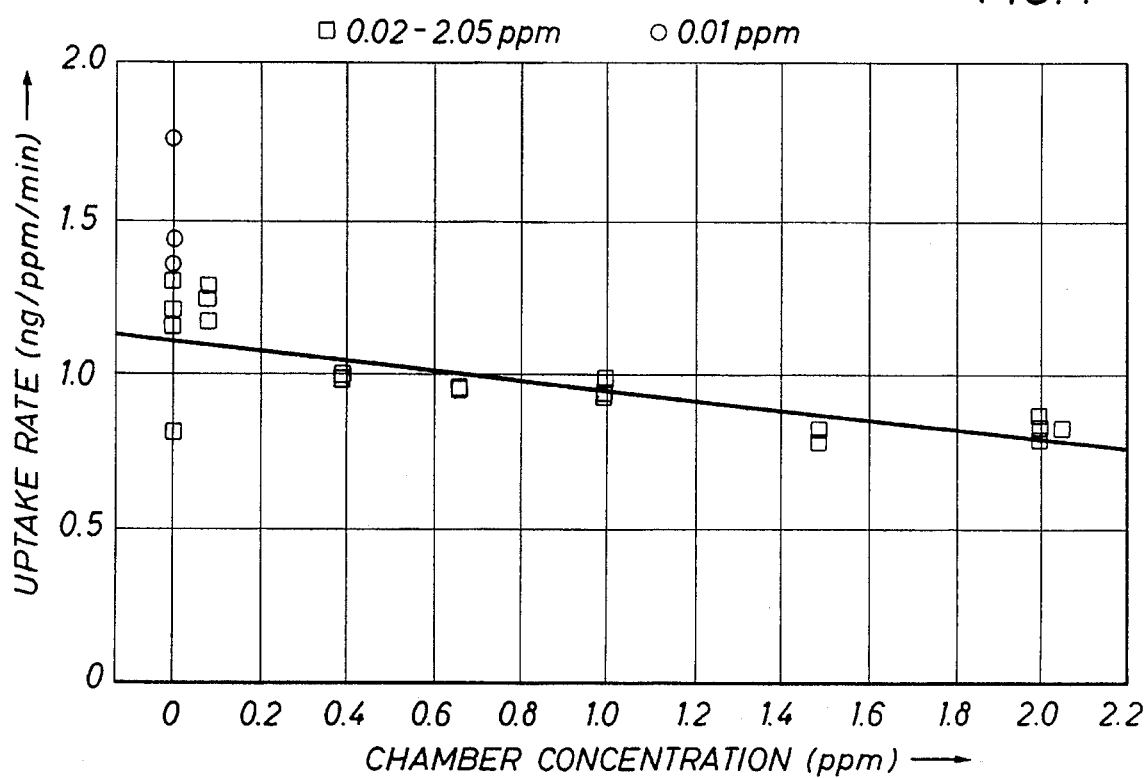
FIG. 4 is a graph of the linear regression for the benzene uptake rate as a function of exposure chamber concentration. The thermally desorbable dosimeter was subjected to a stable gas concentration containing benzene at different levels between 0.01 and 2.05 ppm. The uptake rate was measured at these levels under different relative humidity and linear face velocity conditions.
Figure 5:
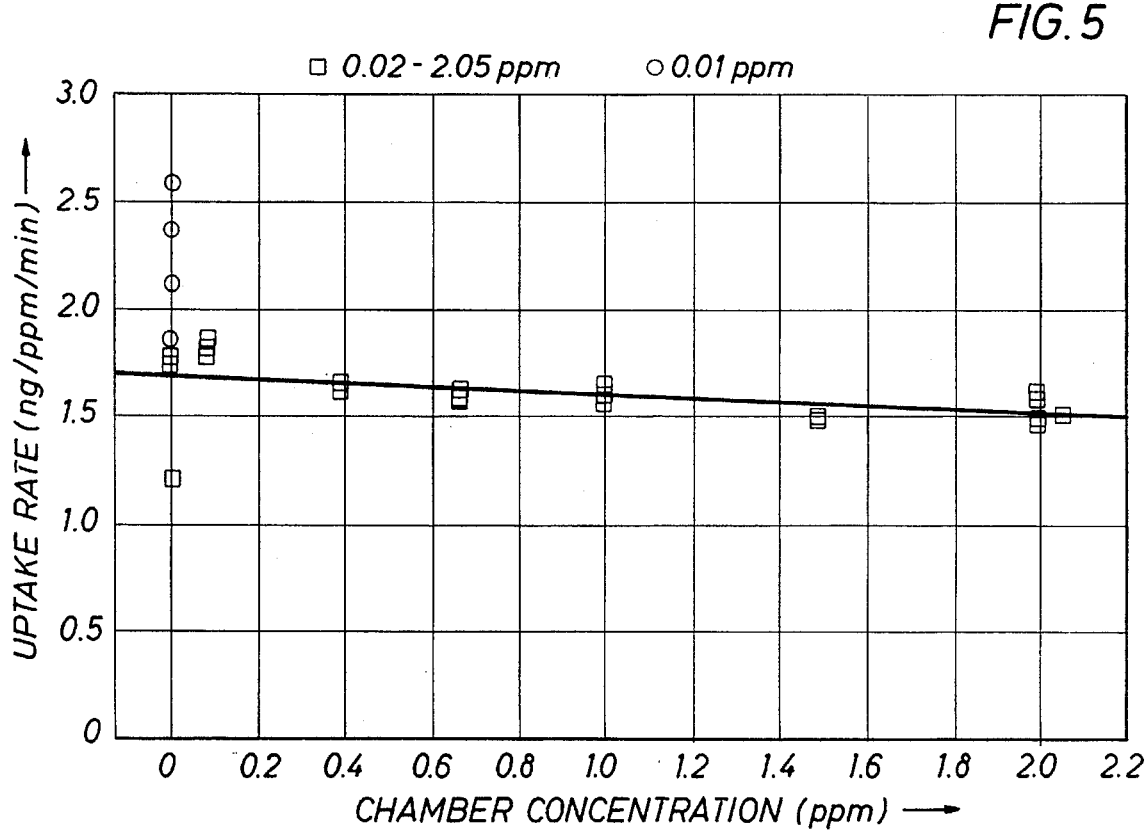
FIG. 5 is a graph of the linear regression for the toluene uptake rate as a function of exposure chamber concentration. The thermally desorbable dosimeter was subjected to a stable gas concentration containing toluene at different levels between 0.01 and 2.05 ppm. The uptake rate was measured at these levels under different relative humidity and linear face velocity conditions.
Figure 6:
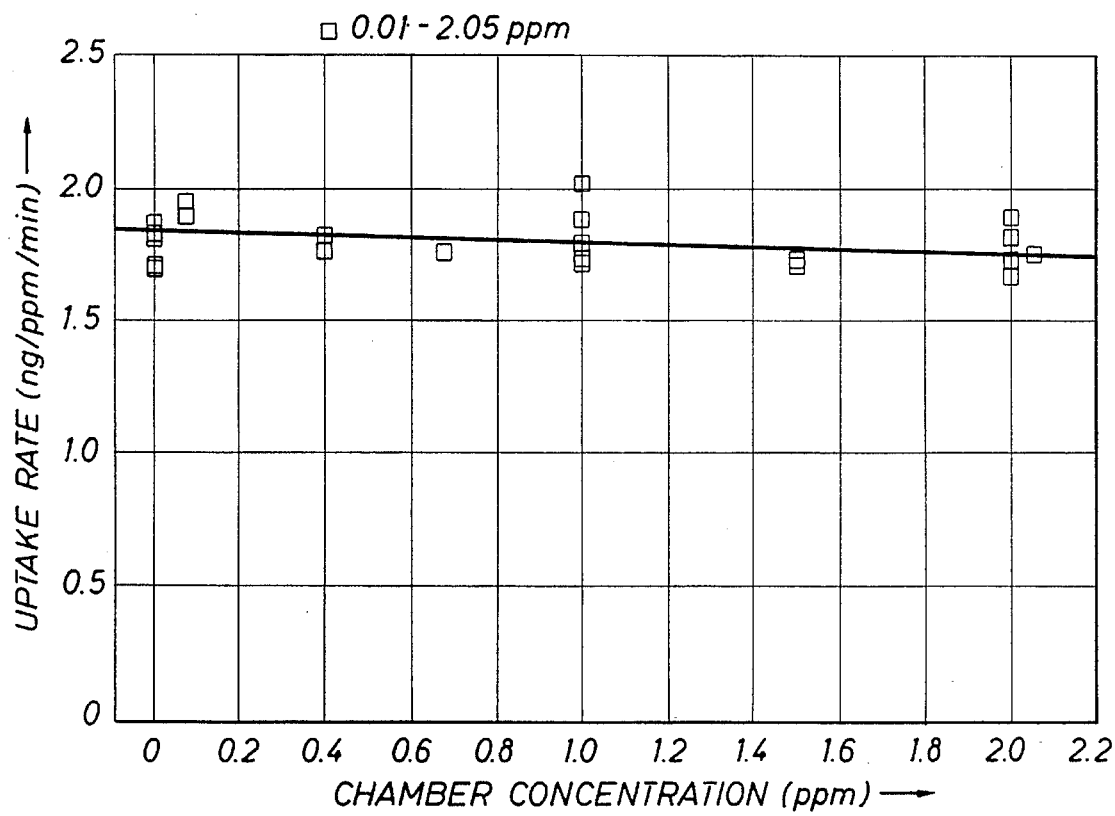
FIG. 6 is a graph of the linear regression for the ethylbenzene uptake rate as a function of exposure chamber concentration. The thermally desorbable dosimeter was subjected to a stable gas concentration containing ethylbenzene at different levels between 0.01 and 2.05 ppm. The uptake rate was measured at these levels under different relative humidity and linear face velocity conditions.
Figure 7:
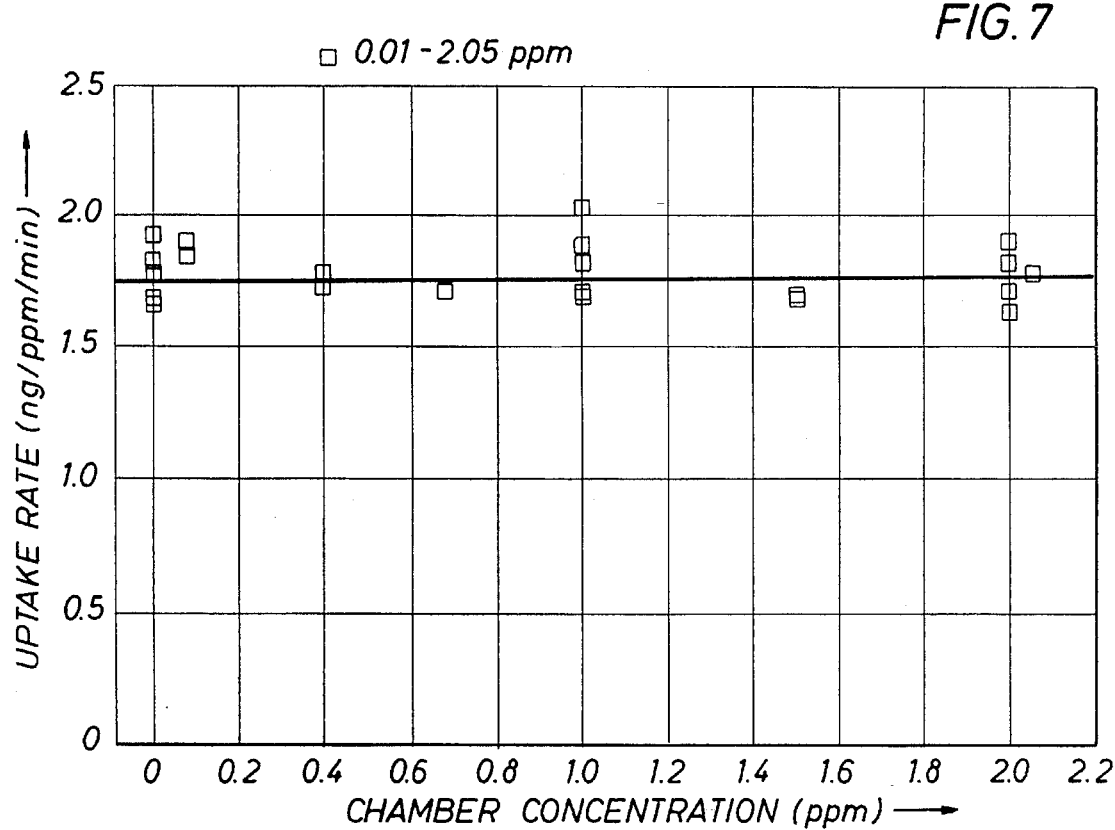
FIG. 7 is a graph of the linear regression for the m-xylene uptake rate as a function of exposure chamber concentration. The thermally desorbable dosimeter was subjected to a stable gas concentration containing m-xylene at different levels between 0.01 and 2.05 ppm. The uptake rate was measured at these levels under different relative humidity and linear face velocity conditions.
Figure 8:
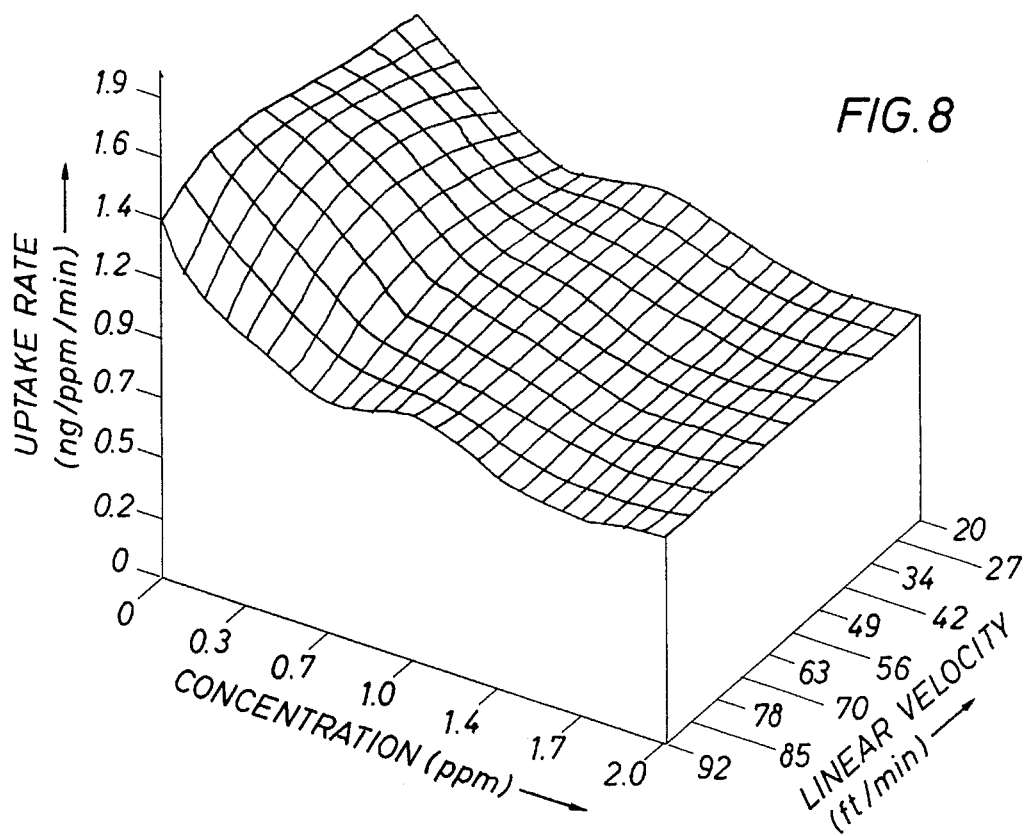
FIG. 8 is a three-dimensional graph illustrating the interaction between concentration and linear face velocity in determining the uptake rate for benzene. A plane or level surface indicates that varying these parameters has little effect on determining the uptake rate.
Figure 9:
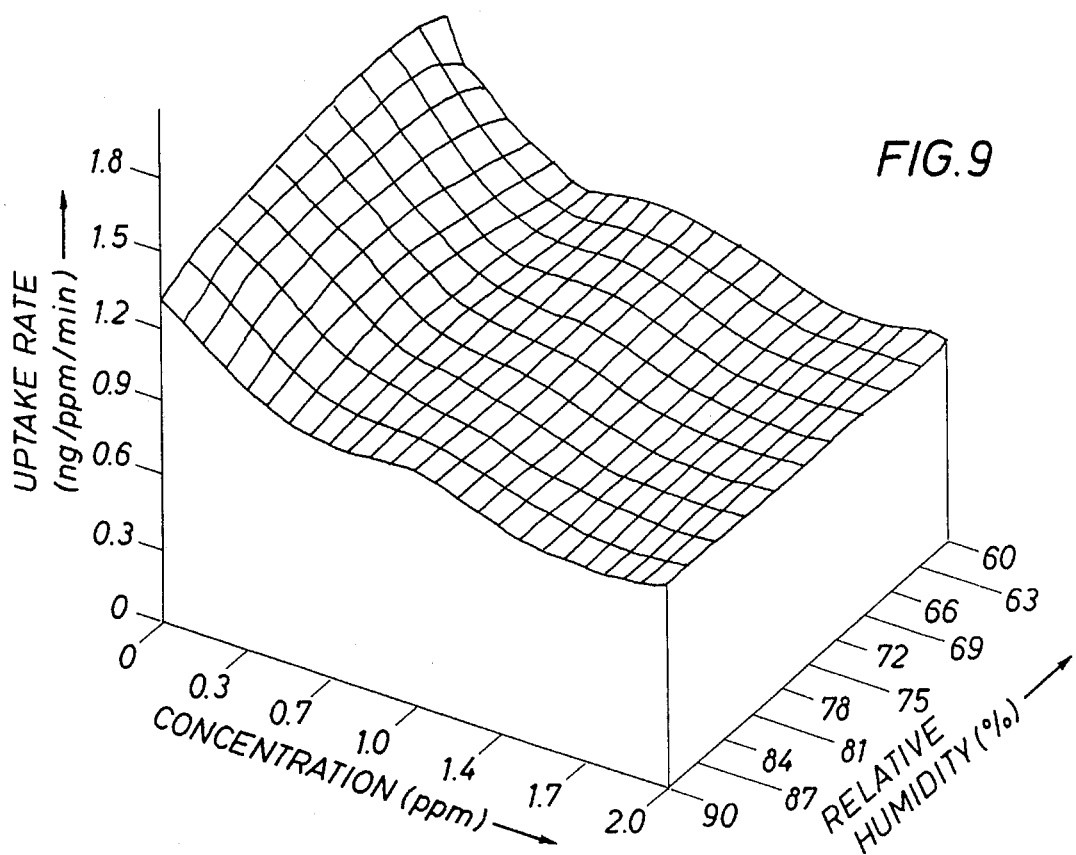
FIG. 9 is a three-dimensional graph illustrating the interaction between concentration and relative humidity in determining the uptake rate for benzene. A plane or level surface indicates that varying these parameters has little effect on determining the uptake rate.
Figure 10:
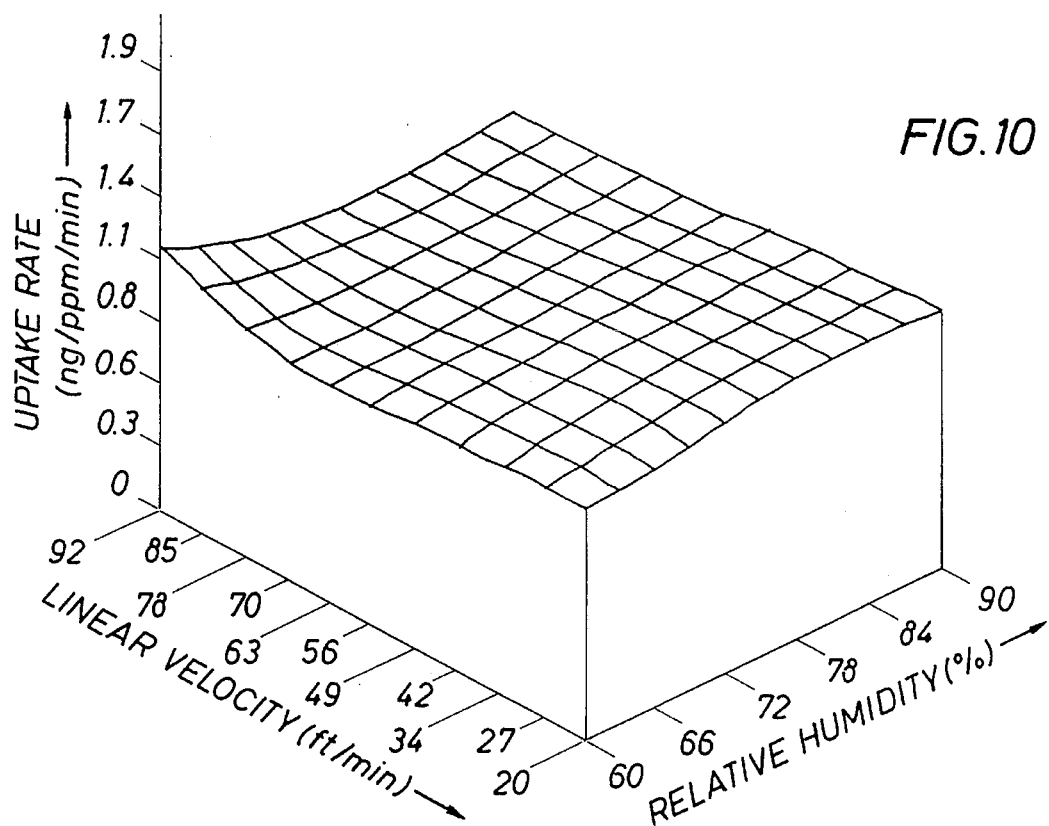
FIG. 10 is a three-dimensional graph illustrating the interaction between linear face velocity and relative humidity at all concentrations in determining the uptake rate for benzene. A plane or level surface indicates that varying these parameters has little effect on determining the uptake rate.
Figure 11:
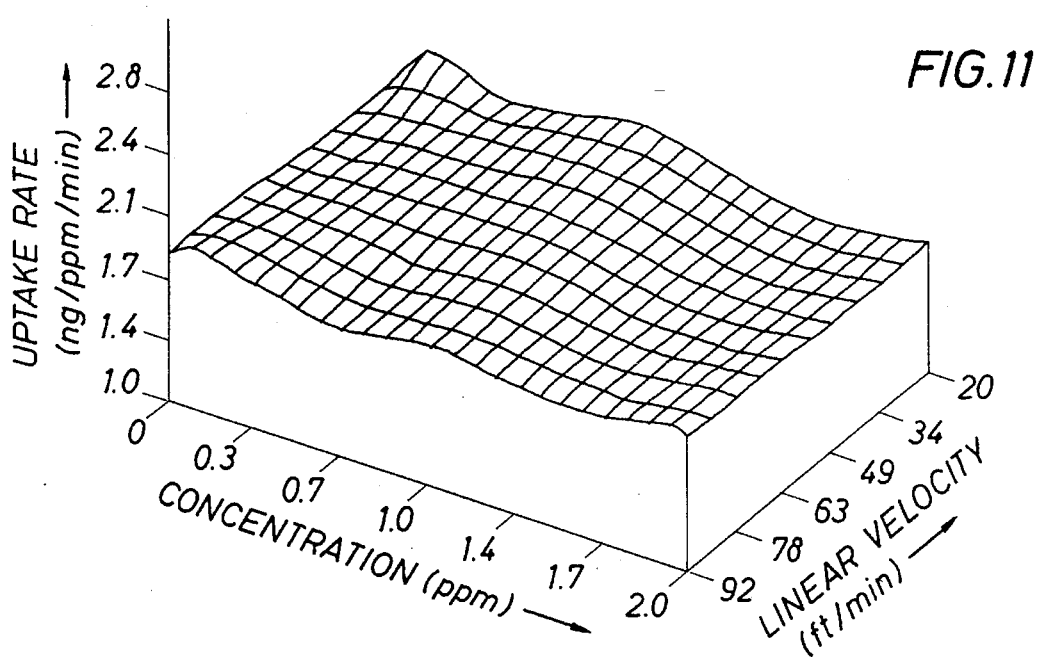
FIG. 11 is a three-dimensional graph illustrating the interaction between concentration and linear face velocity in determining the uptake rate of ethylbenzene. A plane or level surface indicate that varying these parameters has little effect on determining the uptake rate.
Figure 12:
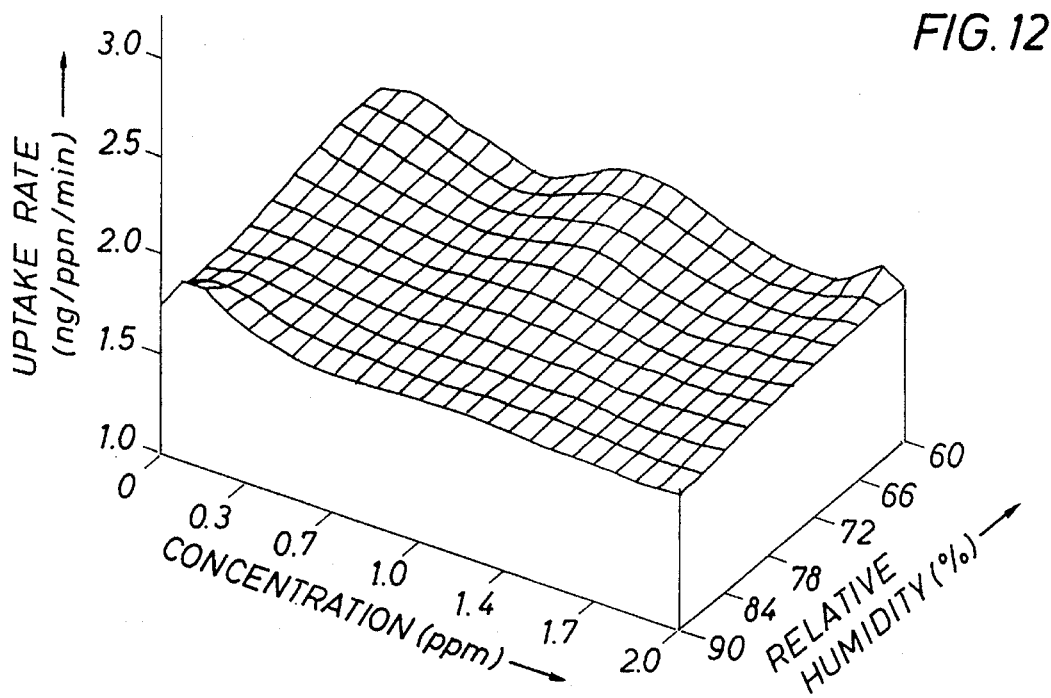
FIG. 12 is a three-dimensional graph illustrating the interaction between concentration and relative humidity in determining the uptake rate for ethylbenzene. A plane or level surface indicates that varying these parameters has little effect on determining the uptake rate.
Figure 13:
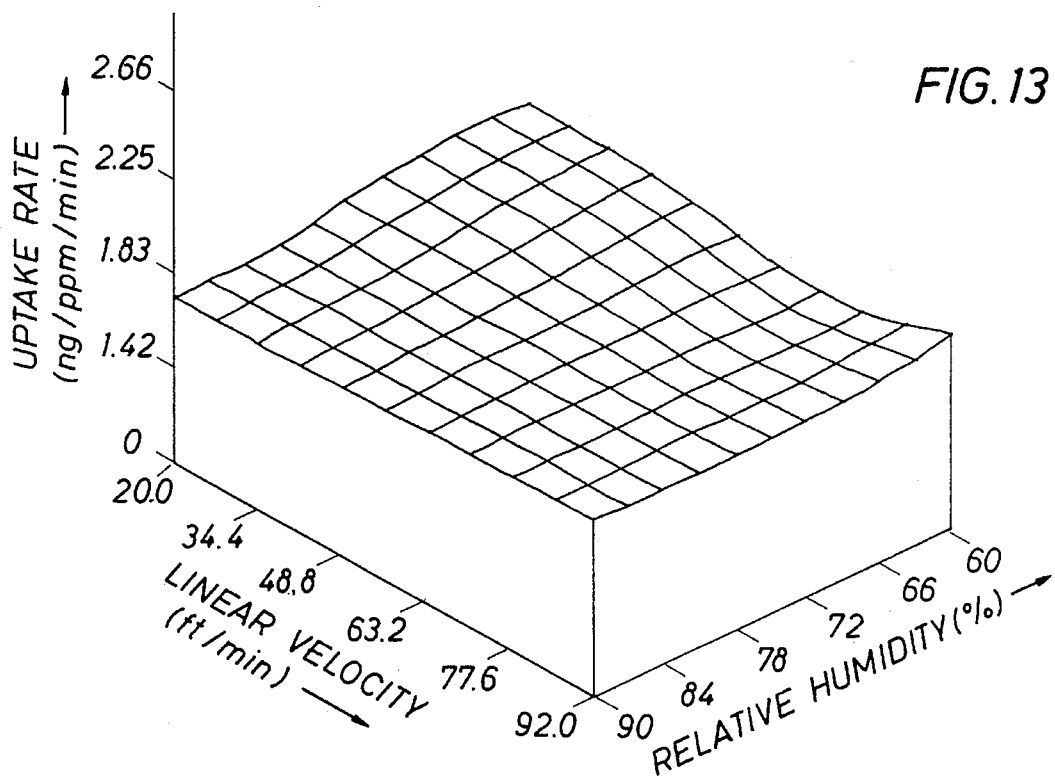
FIG. 13 is a three-dimensional graph illustrating the interaction between linear face velocity and relative humidity at all concentrations in determining the uptake rate for ethylbenzene. A plane or level surface indicates that varying these parameters has little effect on determining the uptake rate.

The passive dosimeter (ATD tube) is illustrated generally at 10 in FIG. 1. The dosimeter 10 preferably comprises a 0.2 cm$^2$ (0.50 cm diameter) TENAX pellet 20, weighing from 3–10 mg, preferably about 4 mg, sandwiched between two small pieces of 100 mesh stainless steel wire gauze screen 22, 24 as shown in more detail in FIG. 2. The diffusion length of the dosimeter is about 1.5 cm. The pellet 20 is formed by pressing the sorbent material 26 between the two stainless steel wire screens 22, 24 in a punch and die press 40 shown in FIG. 3. Before using the newly fabricated die, it should be washed with deionized water, degreased with acetone and washed again with deionized water. The press 40 with plungers 42 and 46 is then placed as shown in FIG. 3. A 100 mesh stainless steel wire gauze 22 is placed inside the die 44 so as to rest on plunger 46. Four milligrams of TENAX-TA sorbent material 26 is weighed on an analytical balance and poured into the die 44 to rest on top of the wire gauze 22. A second wire gauze 24 is then placed on top of the sorbent material 26 and plunger 42 is then placed into the die. The entire assembly 40 is then pressed together on a small laboratory vise. Tests at different pressures showed that pressure is not critical as long as the gauze/sorbent/gauze assembly is compacted into an integral body. The integrated formed pellet 20 is removed from the die 44 by use of the plunger 48 and then inserted into the dosimeter tube 10 with a loading device (not shown) purchased from the Perkin-Elmer Co. The pellet 20 may be 1–4 mm in thickness, preferably about 1 mm. This thin wafer sorbent material design also significantly decreases the GC background level associated with the thermal desorption analysis. The sorbent material 26 is preferably made of a porous polymer material based on 2,6-diphenyl-p-phenylene oxide and sold under the trademark TENAX.

After exposure to the test atmosphere in a controlled atmosphere exposure chamber for 6 hours, the passive dosimeters are thermally desorbed on e.g., a Perkin-Elmer Model ATD-400 Automatic Thermal Desorption System and analyzed by a GC with a 60 meter boiling point capillary column (such as a DB-1) and a flame ionization detector.

A seven-component test atmosphere was used for testing the dosimeter. The components used were methyl tert-butyl ether (MTBE), diisopropyl ether (DIPE), benzene, toluene, ethyl benzene, m-xylene and n-heptane. The exposure chamber relative humidity was controlled at various levels between 60–90% and the surface linear velocity of the gas stream in front of the dosimeter was maintained at various values between 20–90 ft/min. The composition and concentration of the gas atmosphere in the chamber was controlled through two massflow controllers and monitored with a Photovac Model 10S50 gas chromatograph with a CPSIL 19 CB isothermal GC column (10 meter) and a photoionization detector (GC/PID).

Sixteen passive dosimeters were subjected to various exposure chamber concentrations (ppm) of MTBE, DIPE, benzene, toluene, ethyl benzene, m-xylene and n-heptane for 6 hours. The thermal desorption and subsequent GC analyses of the passive dosimeters were carried out immediately after the exposure test. For comparison, eight charcoal tubes (Lot No. 226-01, SKC Co.) were simultaneously exposed to the above test conditions. These charcoal tubes were desorbed using $CS_2$ and analyzed with a gas chromatograph equipped with a flame ionization detector according to NIOSH Method 1501. Table 1 lists the experimental design used to evaluate the performance of the TENAX wafer thermal desorbable dosimeters in the exposure chamber. As can be seen from the table, combinations of three levels of relative humidity and three levels of linear face velocity were used for the exposure chamber test.

TABLE 1

Experimental Design of the TENAX Wafer Passive Dosimeter Test

| PPM | RH (%) | 90 | 60 | 70 | 60 | 90 | 60 |
|---|---|---|---|---|---|---|---|
|  | FV (ft/min) | 90 | 90 | 70 | 70 | 20 | 20 |
| 0.01 |  | X | X |  |  | X | X |
| 0.02 |  | X | X |  |  | X | X |
| 0.1 |  | X | X |  |  | X | X |
| 0.4 |  |  | X |  |  | X |  |
| 0.7 |  |  |  | X | X |  |  |
| 1.0 |  | X | X |  |  | X | X |
| 1.5 |  | X |  |  |  |  | X |
| 2.0 |  | X | X |  |  | X | X |

RH- RELATIVE HUMIDITY (%); FV--face velocity (ft/min)

Table 2 lists the results of the chromatographic analysis for benzene, toluene, ethylbenzene and m-xylene from exposure tests. The table lists the average concentration of each component obtained from the 16 tested TENAX wafer passive dosimeters and 8 SKC active charcoal tube monitors. The latter SKC monitors also served to verify the exposure chamber concentrations.

TABLE 2

Gas Chromatographic Results of TENAX Wafer Dosimeter Tests

| Chamber (ppm) | RH | FV | BZ Tx (ppm) | BZ SKC (ppm) | Tol Tx (ppm) | Tol SKC (ppm) | E-BZ Tx (ppm) | E-BZ SKC (ppm) | Xyl Tx (ppm) | Xyl SKC (ppm) |
|---|---|---|---|---|---|---|---|---|---|---|
| 0.01 | 60 | 20 | 0.016 | 0.008 | 0.011 | 0.007 | 0.010 | 0.006 | 0.010 | 0.006 |
| 0.01 | 60 | 90 | 0.021 | 0.008 | 0.015 | 0.007 | 0.011 | 0.005 | 0.011 | 0.006 |
| 0.01 | 90 | 20 | 0.016 | 0.011 | 0.013 | 0.010 | 0.010 | 0.009 | 0.010 | 0.009 |
| 0.01 | 90 | 20 | 0.017 | 0.011 | 0.012 | 0.011 | 0.009 | 0.011 | 0.010 | 0.011 |
| 0.02 | 60 | 20 | 0.019 | 0.018 | 0.015 | 0.015 | 0.011 | 0.013 | 0.014 | 0.013 |
| 0.02 | 60 | 90 | 0.029 | 0.016 | 0.022 | 0.015 | 0.020 | 0.014 | 0.020 | 0.014 |
| 0.02 | 90 | 20 | 0.028 | 0.017 | 0.022 | 0.015 | 0.019 | 0.013 | 0.019 | 0.013 |
| 0.02 | 90 | 90 | 0.028 | 0.022 | 0.033 | 0.020 | 0.030 | 0.022 | 0.020 | 0.021 |
| 0.10 | 60 | 20 | 0.135 | 0.105 | 0.111 | 0.090 | 0.105 | 0.074 | 0.108 | 0.073 |
| 0.10 | 60 | 90 | 0.133 | 0.090 | 0.115 | 0.088 | 0.107 | 0.079 | 0.107 | 0.080 |
| 0.10 | 90 | 20 | 0.132 | 0.096 | 0.113 | 0.088 | 0.105 | 0.077 | 0.105 | 0.078 |
| 0.10 | 90 | 90 | 0.125 | 0.110 | 0.113 | 0.100 | 0.107 | 0.098 | 0.108 | 0.099 |
| 0.40 | 90 | 90 | 0.423 | 0.381 | 0.406 | 0.372 | 0.390 | 0.368 | 0.395 | 0.391 |
| 0.40 | 60 | 90 | 0.427 | 0.382 | 0.411 | 0.364 | 0.402 | 0.360 | 0.407 | 0.362 |
| 0.70 | 70 | 70 | 0.703 | 0.630 | 0.691 | 0.603 | 0.678 | 0.596 | 0.685 | 0.596 |
| 0.70 | 60 | 70 | 0.654 | 0.707 | 0.627 | 0.709 | 0.608 | 0.677 | 0.617 | 0.684 |
| 0.70 | 60 | 70 | 0.635 | 0.706 | 0.620 | 0.693 | 0.609 | 0.679 | 0.617 | 0.685 |
| 1.00 | 60 | 20 | 1.037 | 1.028 | 1.046 | 0.945 | 1.121 | 0.823 | 1.156 | 0.833 |
| 1.00 | 60 | 20 | 1.025 | 0.922 | 1.028 | 0.851 | 1.007 | 0.778 | 1.037 | 0.764 |
| 1.00 | 60 | 90 | 1.008 | 0.978 | 1.048 | 0.902 | 1.044 | 0.828 | 1.077 | 0.817 |
| 1.00 | 90 | 20 | 0.984 | 0.949 | 0.986 | 0.911 | 0.956 | 0.907 | 0.965 | 0.903 |
| 1.00 | 90 | 90 | 0.992 | 0.982 | 0.988 | 0.887 | 0.964 | 0.866 | 0.974 | 0.868 |
| 1.50 | 60 | 20 | 1.268 | 1.574 | 1.396 | 1.526 | 1.415 | 1.494 | 1.429 | 1.490 |
| 1.50 | 90 | 90 | 1.223 | 1.433 | 1.416 | 1.298 | 1.426 | 1.286 | 1.441 | 1.241 |
| 2.00 | 60 | 20 | 1.716 | 1.939 | 2.003 | 1.829 | 2.011 | 1.709 | 2.081 | 1.687 |
| 2.00 | 60 | 90 | 1.780 | 1.790 | 2.045 | 1.723 | 2.098 | 1.594 | 2.174 | 1.576 |
| 2.00 | 90 | 20 | 1.694 | 1.837 | 1.857 | 1.774 | 1.845 | 1.769 | 1.860 | 1.757 |
| 2.00 | 90 | 90 | 1.624 | 1.945 | 1.882 | 1.758 | 1.925 | 1.713 | 1.946 | 1.715 |
| 2.05 | 60 | 90 | 1.740 | 1.728 | 1.968 | 1.642 | 2.016 | 1.538 | 2.089 | 1.535 |

RH - Relative Humidity (%)
FV - Linear Face Velocity (ft/min.)

The uptake rates for MTBE and DIPE, as well as four aromatic test components with a 1.00 and 0.10 PPM exposure chamber concentration are also summarized in Table 3.

TABLE 3

The Average Mass Loading of TENAX Passive Dosimeters

|  | Unit | MTBE | DIPE | BZ | TOL | E-BZ | XYL |
|---|---|---|---|---|---|---|---|
| Chamber (set) | PPM | 1.00 | 1.00 | 1.00 | 1.00 | 1.00 | 1.00 |
| Photovac (GC) | PPM | 0.936 | 1.021 | 1.084 | 1.050 | 1.051 | 1.067 |
| SKC | PPM | 1.063 | 1.003 | 0.982 | 0.887 | 0.866 | 0.868 |
| TENAX | mg | 0.099 | 0.308 | 0.339 | 0.569 | 0.625 | 0.615 |
| Uptake Rate |  | 0.274 | 0.854 | 0.943 | 1.581 | 1.735 | 1.704 |
| Chamber (set) | PPM | 0.10 | 0.10 | 0.10 | 0.10 | 0.10 | 0.10 |
| Photovac (GC) | PPM | 0.097 | 0.097 | 0.097 | 0.097 | 0.097 | 0.097 |
| SKC | PPM | 0.084 | 0.099 | 0.096 | 0.088 | 0.077 | 0.078 |
| TENAX | mg | 0.018 | 0.043 | 0.045 | 0.065 | 0.068 | 0.066 |
| Uptake Rate |  | 0.503 | 1.181 | 1.256 | 1.811 | 1.886 | 1.842 |

The linear regression analysis of the passive dosimeter vs. the exposure chamber concentrations is listed in Table 4. The linear regression analysis of SKC charcoal tubes is also listed for comparison.

TABLE 4

Linear Regression Analysis of TENAX Wafer Dosimeters

| Regression equation: | Tx (ppm) = a + b Chamber (ppm), Corr Coeff |
|---|---|
| Benzene: | Tx (ppm) = 0.056 + 0.86 Chamber, 0.989 |
| Toluene: | Tx (ppm) = 0.016 + 0.96 Chamber, 0.997 |
| Ethylbenzene: | Tx (ppm) = 0.005 + 0.98 Chamber, 0.996 |
| m-Xylene: | Tx (ppm) = 0.002 + 1.00 Chamber, 0.994 |
| Regression equation: | Tx (ppm) = a + b SKC (ppm), Corr Coeff |
| Benzene: | Tx (ppm) = 0.051 + 0.90 SKC, 0.982 |
| Toluene: | Tx (ppm) = 0.008 + 1.09 SKC, 0.989 |
| Ethylbenzene: | Tx (ppm) = 0.008 + 1.15 SKC, 0.978 |
| m-Xylene: | Tx (ppm) = 0.002 + 1.18 SKC, 0.973 |

Note:
Corr coeff -- Correlation coefficient.
Tx -- TENAX tube analytical concentration.
Chamber -- Exposure chamber concentration.
SKC -- SKC tube analytical concentration.

FIGS. 4–7 plot the uptake rates of four aromatic compounds as a function of the exposure chamber test atmosphere concentrations. As can be seen from these tables and figures, the uptake rates for BTEX are relatively stable over the concentration range tested, except at the lowest test chamber concentration of 0.01 ppm, where relatively high uptake rates were found for benzene.

FIGS. 8–13 show three dimensional example plots of the uptake rates of benzene and ethylbenzene as a function of exposure chamber concentrations, relative humidity and linear face velocity. As can be seen from these plots, both relative humidity and velocity have little effect on the uptake rates. The concentration also has little effect, except at the extremely low concentration tested (~0.01 ppm) where uptake rates tend to be high.

The limit of detection (LOD), which is also called the method detection limit (MDL), is defined as $$MDL = t_{(N-1\ df, 1-\alpha=0.99)} \times S_c \qquad (2)$$

where $t_{(N-1\ df,\ 1-\alpha=0.99)}$ is the Student's t-value for a one-tailed test at the 99% confidence level with N-1 degrees of freedom (df). $S_c$ is the standard deviation of the replicate analysis at concentrations near the detection limit. With replicates of 16 TENAX wafer tubes used for the exposure test at each concentration, the t-value is 2.602. Consequently, the average detection limit of TENAX-TA dosimeters for benzene, toluene, ethylbenzene and xylene using the exposure chamber concentrations at 0.01 and 0.02 ppm can be calculated as 0.004, 0.004, 0.003 and 0.003 ppm, respectively. Similarly, the calculated detection limits for MTBE and DIPE are both 0.01 ppm.

The use of the new passive dosimeter coupled with thermal desorption analysis eliminates both the use of sampling pumps and solvent extraction procedures for BTEX determination by simplifying the sampling and analysis process for BTEX occupational monitoring.

The wafer/sorbent material design significantly reduces the GC background signal caused by the thermal desorption of the sorbent material and enhances the detectability of the dosimeter for very low concentrations (~0.005–0.01 ppm time-weighted-average for 8 hour exposure monitoring) of air contaminants.

The thin wafer design and small amount of sorbent material used also enhances the thermal desorption behavior of the dosimeter and reduces the analysis time significantly.

The pressed TENAX/stainless-steel-gauze wafer also ensures a very smooth diffusion surface for the sorbent material and produces a much tighter analytical variation. The integration of the stainless steel wire gauze with TENAX also significantly increases the mechanical strength of the wafer and makes loading/unloading the sorbent material from the passive dosimeter much easier.

The described thermally desorbable dosimeters can be used for personal exposure assessment of aromatic hydrocarbons, MTBE, and DIPE. The dosimeter can be simply clipped to the upper pockets or collar near the breathing zone for designated sampling time or shift time. The sampled dosimeter should then be capped with the storage caps and stored and shipped to the analytical lab for analysis. If sampling for the more volatile organic compounds, such as MTBE and DIPE, the shipping and storage of the dosimeters should follow the current standard industrial hygiene practice, i.e. under refrigerated conditions (such as dry ice). The device is best suited for the time weighted average (TWA) assessment. The short term exposure level (STEL) use is possible but caution should be taken to avoid the overestimation of the exposure level.

While the invention has been described using the preferred sorbent material TENAX compressed into a pellet, it will be apparent to those skilled in the art that other sorbent materials may be used depending upon the contaminant to be tested. For example, a dosimeter could comprise a pellet comprised of either various phases (solid or liquid) of chromatographic sorbents on diatomaceous earth, porous polymer sorbents, synthetically produced potassium, sodium, or calcium forms of zeolites, activated carbon, or a synthetic spherical silica-based synthetic support with various chromatographic stationary phases bonded to it.

Likewise, although stainless steel is the preferred material for the wire gauze, other inert metals may be used.

What is claimed is:

1. A passive dosimeter adapted for thermal desorption analysis comprising:

a hollow dosimeter tube into which gases can diffuse;

a thermally desorbable sorbent material compressed into a wafer, said sorbent material weighing between about 3 and about 10 milligrams;

a piece of wire gauze on each side of said wafer, said pieces of wire gauze compacted into an integral body with said sorbent material to form an integrated sorbent material pellet;

said integrated sorbent material pellet positioned transversely within said hollow dosimeter tube.

2. The dosimeter of claim 1 wherein said sorbent material is a porous polymer material based on 2,6-diphenyl-p-phenylene oxide.

3. The dosimeter of claim 1 wherein said sorbent material is selected from the group consisting of solid phase chromatographic sorbents on diatomaceous earth, liquid phase chromatographic sorbents on diatomaceous earth, porous polymer sorbents, synthetically produced potassium zeolites, synthetically produced sodium zeolites, synthetically produced calcium zeolites, activated carbon, and synthetic spherical silica-based supports having a chromatographic stationary phase bonded thereto.

4. The dosimeter of claim 1 wherein said wire gauze is made of stainless steel.

5. The dosimeter of claim 1 wherein said sorbent material weighs about 4 milligrams.

6. The dosimeter of claim 1 wherein said pellet is about 1 millimeter in thickness.

7. The dosimeter of claim 1 wherein said pellet is between 1–4 millimeters in thickness.

8. The dosimeter of claim 1 wherein said wire gauze is made of an inert metal.

* * * * *